United States Patent [19]

Takahashi et al.

[11] Patent Number: 4,752,862
[45] Date of Patent: Jun. 21, 1988

[54] ELECTRONIC DEVICE

[75] Inventors: Akio Takahashi; Hitoshi Ochiai, both of Tokyo, Japan

[73] Assignee: Seiko Instruments & Electronics Ltd., Tokyo, Japan

[21] Appl. No.: 905,338

[22] PCT Filed: Dec. 20, 1985

[86] PCT No.: PCT/JP85/00697

§ 371 Date: Oct. 8, 1986

§ 102(e) Date: Oct. 8, 1986

[87] PCT Pub. No.: WO86/03910

PCT Pub. Date: Jul. 3, 1986

[30] Foreign Application Priority Data

Dec. 21, 1984 [JP] Japan ................ 59-270362
Nov. 12, 1985 [JP] Japan ................ 60-253119
Nov. 12, 1985 [JP] Japan ................ 60-253120
Nov. 13, 1985 [JP] Japan ................ 60-254552
Nov. 13, 1985 [JP] Japan ................ 60-254553

[51] Int. Cl.[4] .................. H05K 7/10; H01R 9/00; H05F 3/00
[52] U.S. Cl. .................. 361/403; 361/212; 361/406
[58] Field of Search .................. 361/212, 403, 406

[56] References Cited

U.S. PATENT DOCUMENTS 4,557,379 12/1985 Lane et al. ................ 361/212
4,580,193 4/1986 Edwards ................ 361/403
4,617,471 10/1986 Suzuki ................ 361/406

OTHER PUBLICATIONS

Mims, Forrest M., Engineer's Notebook, Radio Shack, 1979, pp. 105, 113.

Primary Examiner—L. T. Hix
Assistant Examiner—David Porterfield
Attorney, Agent, or Firm—Bruce L. Adams; Van C. Wilks

[57] ABSTRACT

Art to make the electronic devices immune against the static electricity, so that the circuits are not erroneously operated or broken down by the electric field, by the electromagnetic waves or by the flow of electric charge. In an electronic device which is not grounded, the capacity between an active side 2 and an input line 4 is selected to be smaller than the capacity between a pull side 3 and the input line 4 relying upon the layout of IC pads, relying upon the layout of circuit board patterns, or relying upon the capacitors, and a metal housing is not connected to the active side 2. The electronic device exhibits perfect immunity against the flow of electric charge into the circuit network caused by the discharge of static electricity, against the noise caused by the electromagnetic waves having high energy, and against the electric field where the electric discharge is not taking place, i.e., the electronic device exhibits immunity against all of the phenomena of static electricity.

5 Claims, 7 Drawing Sheets

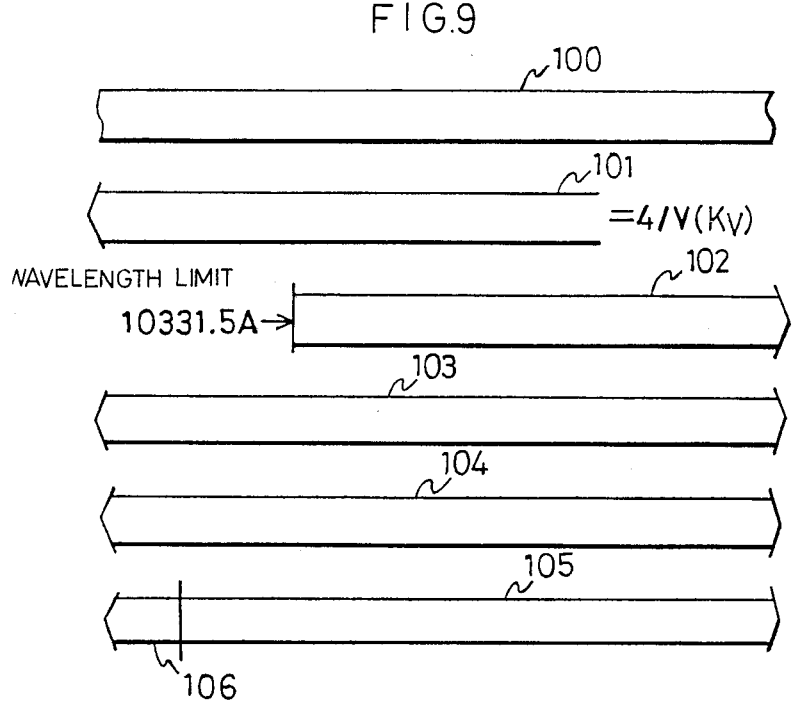
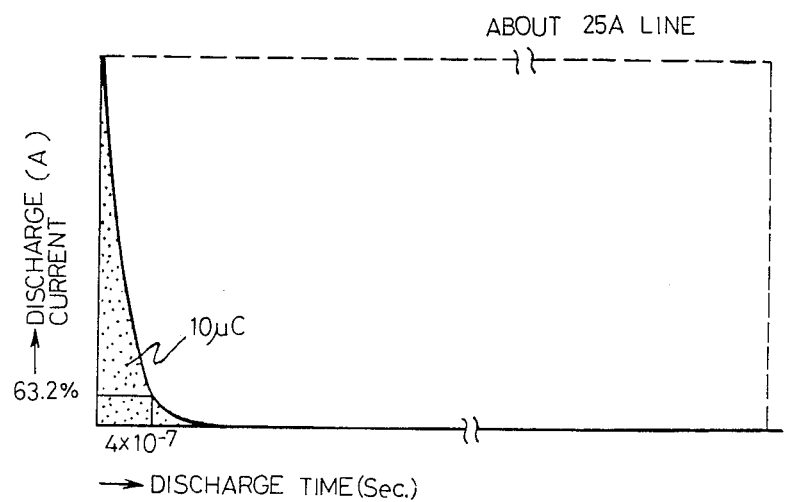

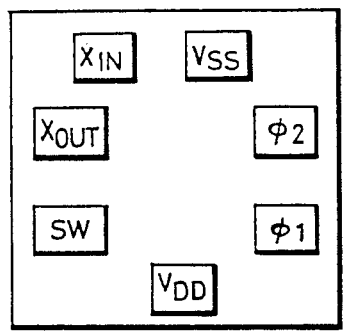
FIG.11
FIG.12
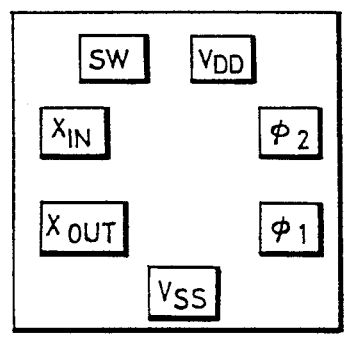
FIG.13
FIG.14
FIG.15
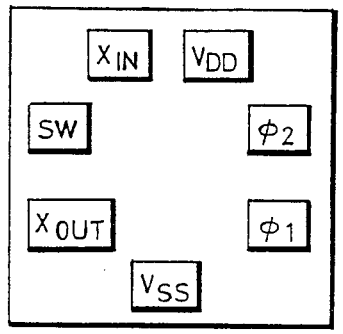
FIG.16

|  | $X_{IN}$ | $X_{OUT}$ | $\phi_1$ | $\phi_2$ | SW | $V_{DD}$ | $V_{SS}$ |
|---|---|---|---|---|---|---|---|
| $X_{IN}$ |  | ○ |  |  |  | ○ |  |
| $X_{OUT}$ | ○ |  |  |  | ○ |  |  |
| $\phi_1$ |  |  |  | ○ |  |  | ○ |
| $\phi_2$ |  |  | ○ |  |  | ○ |  |
| SW |  | ○ |  |  |  |  | ○ |
| $V_{DD}$ | ○ |  |  | ○ |  |  |  |
| $V_{SS}$ |  |  | ○ |  | ○ |  |  |

|  | $X_{IN}$ | $X_{OUT}$ | $\phi_1$ | $\phi_2$ | SW | $V_{DD}$ | $V_{SS}$ |
|---|---|---|---|---|---|---|---|
| $X_{IN}$ |  | ○ |  |  | ○ |  |  |
| $X_{OUT}$ | ○ |  |  |  |  | ○ |  |
| $\phi_1$ |  |  |  | ○ |  | ○ |  |
| $\phi_2$ |  |  | ○ |  |  |  | ○ |
| SW | ○ |  |  |  |  |  | ○ |
| $V_{DD}$ |  | ○ | ○ |  |  |  |  |
| $V_{SS}$ |  |  |  | ○ | ○ |  |  |

|  | $X_{IN}$ | $X_{OUT}$ | $\phi_1$ | $\phi_2$ | SW | $V_{DD}$ | $V_{SS}$ |
|---|---|---|---|---|---|---|---|
| $X_{IN}$ |  | ● |  |  |  | ○ |  |
| $X_{OUT}$ | ● |  |  |  | ○ |  |  |
| $\phi_1$ |  |  |  | ● |  |  | ○ |
| $\phi_2$ |  |  | ● |  |  | ○ |  |
| SW | ○ |  |  |  |  |  | ● |
| $V_{DD}$ |  | ○ | ○ |  |  |  |  |
| $V_{SS}$ |  |  |  | ○ | ● |  |  |

ELECTRONIC DEVICE

TECHNICAL FIELD

The present invention relates to structures for preventing portable small electronic devices and small data devices from being erroneously operated or from being broken down by static electricity.

BACKGROUND ART

Portable electronic devices such as IC cards, cameras, wristwatches, and those electronic devices that are not grounded, are prone to be erroneously operated or broken down due to the phenomenon of static electricity.

Such devices have heretofore been prevented from malfunctioning, either by erroneously operating or from breaking down, in the same manner as those electronic devices that can be usually grounded. Using a reference potential of a grounding circuit, however, the noise can be suppressed efficiently over a frequency region which is lower than that of the VHF band. Even if one point or more points are grounded, the grounding circuit is not quite effective to absorb the electromagnetic waves of large energy that are generated when the static electricity is discharged. Therefore, the noise must be suppressed in another manner.

Many examples to cope with this problem have been introduced in, for example, Electronics System, "Materials To Cope With Troubles Caused by Static Electricity" compiled by Norio Murasaki, entitled "Section 6, Countermeasures 5.6.2.3 Against Static Electricity in ECR, Electronic Circuit and Printed Board", pp. 222-224. However, many technicians are empirically aware of the fact that there is no simple method which offers sufficiently desirable effects. It has been attempted to absorb noise by extending the pattern of the ground side of the circuit board having the potential of the active side 2 or to increase the width of the pattern, or by a method taught in "Grounding of Housing", p. 84, "Practical Method of Decreasing Noise", Henry W. OTT., Bell Laboratory, U.S.A., translated by Takao Matsui. With the portable electronic devices which are not allowed to be grounded, however, noise is not emitted to the ground, and the concept of grounding cannot be pursued. In the electronic devices that cannot be grounded, a pattern of circuit board of a potential of the active side, that is formed to absorb noise, works as an antenna, and the structure connected to the potential of the active side of the metal housing to accomplish the grounding, works as an antenna. That is, with the pattern of circuit board that is not grounded or with the structure connected to the potential of the active side of the metal housing to accomplish the grounding, the electromagnetic waves are absorbed and are converted into eddy current to produce noise in the circuit network. Furthermore, under the condition where the electric charge is not discharged, the lines assuming the potential of the active side a of floated ground function to increase the difference of electric field distribution relative to the pull side. This becomes a cause of erroneous operation for field effect IC's.

As shown in FIG. 7, under such circumstances, three lines, i.e., an active side or power source line 2, an input line 4 and a pull side or ground line 3 establish an electrically important relationship. Described hereinbelow are the drawbacks that were not solved by the conventional art. For convenience of description, the high potential side of the power supply, whether positive or negative, is referred to as the active side or the power source line 2, and the low potential side is referred to as the pull side or the ground line 3.

FIG. 7 is a circuit diagram which schematically illustrates an input circuit. Here, a capacity or capacitance Ca exists between the active side 2 and the input line 4, and a capacity or capacitance Cp exists between the pull side 3 and the input line 4. The relationship Ca>Cp will be described. It is obvious that electromagnetic waves generated by static electricity or the like are simultaneously superposed as an impulse on the active side 2 and on the pull side 3 of the power source voltage. Therefore, the potential appearing on the input line 4 forms a potential on the active side 2 via Ca. With a relationship Ca>Cp being maintained, a potential on the pull side 3 also appears on Cp but a potential on the active side 2 appears on Ca. As a result, the potential on the input line 4 appears on Ca by an amount that corresponds to the difference between the potential on the pull side 3 and that on the active side 2. Accordingly, even if the switch SW is not turned on, the potential of the input line 4 produces a potential on the active side 2. Under this condition, the input circuit operates erroneously even when the switch SW is not operated. A resistance Rp is provided to form pull means, and a circuit 1 is provided in a stage which succeeds the switch SW.

FIG. 8 is a diagram of voltage waveforms that change with the lapse of time, and illustrates erroneous operations of the input circuit of FIG. 7 caused by the static electricity and the like, and wherein $V_1$ denotes an active potential, $V_2$ denotes a pull potential, $V_3$ denotes a potential of the input line which is usually equal to $V_2$, $V_T$ denotes a threshold potential of the circuit 1 under the ordinary condition which is equal to $V_2/2$, t denotes a time, $t_0$ denotes a time at a moment when $V_0$ which is the power source voltage is rapidly changed by the static electricity into $V_2(t_0)$, $V_2(t_0)$ denotes a potential at the time $t_0$, $V_3(t_0)$ denotes a potential of the input line that is obtained by dividing $V_2(t_0)$ by the capacities Ca and Cp, i.e., $V_2(t_0) \cdot Cp/(Ca+Cp)$, $V_T(t_0)$ denotes a threshold potential of the circuit 1, i.e., $V_2(t_0)/2$, $V_2(t)$ denotes a power source voltage which is given as a function of the time t, and its time constant is nearly equal to C.r where C denotes a resultant capacity consisting of capacities Ca, Cp, and a capacity of noise source, and r denotes an internal resistance of the power source, $V_3(t)$ denotes a potential of the input line 4 given as a function of the time t, i.e., given by $V_3(t) \simeq V_2(t) \cdot Cp/(Ca+Cp) \exp[-t/(CapRp)]$, and its time constant is nearly equal to Cap.Rp which is a product of the resultant capacity Cap consisting of the capacities Ca, Cp and the resistance Rp of the pull means (usually, Rp is considerably greater than r), and $V_T(t)$ denotes a threshold potential $V_2(t)/2$ of the circuit 1 given as a function of the time t.

The device will be described in more detail in conjunction with FIGS. 7 and 8. A man who is electrically charged may produce a voltage in excess of 10 Kv presenting a serious problem in handling electronic devices or portable electronic devices that are not permitted to be grounded. Here, if the potential $V_2$ rapidly increases to $V_2(t_0)$ at the time $t_0$ due to noise in the form of electromagnetic waves produced by the electric discharge, the threshold potential $V_T=V_2/2$ of the circuit 1 changes into $V_T(t_0)=V_2(t_0)/2$, and the potential $V_3=V_2$ of the input line 4 changes into $V_2(t_0)=V_2+[V_2(t_0)-V_2]\cdot Cp/(Ca+Cp)$. If the capacities have a relation $Ca>Cp$, the potential $V_3(t_0)$ of the input line 4 is apt to reach the threshold voltage $V_T(t_0)=V_2(t_0)/2$ depending upon the magnitude of $V_2(t_0)$ and is changed by electromagnetic wave noise so that it becomes an erroneous input. For instance, if the capacities have a relation $Ca=1.5Cp$, the potential $V_2(t_0)$ become more than 6 times as great as the potential under the ordinary condition of the potential $V_2$. If $Ca=4\ Cp$, $V_2(t_0)$ becomes more than 8/3 as great as $V_2$, whereby the potential $V_3(t_0)$ of the input line 4 reaches the threshold voltage $V_T(t_0)=V_2(t_0)/2$ to form an erroneous input.

The above way of thinking is supported by means for deriving a hypothesis that will be described below, and by experiment and investigation using practical electronic devices. Described below are the concept for improving the immunity against static electricity, means for deriving the hypothesis, and experimentation to prove the hypothesis.

(i) Concept

FIG. 9 is a schematic diagram related to energy of the electromagnetic waves and noise, wherein reference numeral 100 denotes a region which includes all of the electromagnetic waves such as VHF electromagnetic waves, infrared rays, visible rays, ultraviolet rays, and X-rays. The electric discharge is a phenomenon of an avalanche of electrons in which the electrons having a kinetic energy proportional to the voltage impinge upon an opposing metal electrode. Most of the electric charge migrates. The electric charge flows through paths having small impedances. Here, what is important is to construct the device so that the electric charge does not pass through the electronic circuit network. Upon impingement, the kinetic energy E is converted into electromagnetic waves. The kinetic energy E of an electron is given by, $$E=\tfrac{1}{2}mv^2=eV$$

The energy is conserved and is converted into electromagnetic waves, i.e., $$eV=h\nu,\ eV=hc/\lambda$$

The wavelength $\lambda$ becomes a minimum at a point where the charged voltage V is a maximum, i.e., $$\lambda\text{min}=hc/eV\text{max}$$

If $$\begin{pmatrix} h: & 6.625\times 10^{-27}\ \text{erg}\cdot\text{sec} \\ c: & 2.9979\times 10^8\ \text{m}\cdot\text{sec}^{-1} \\ e: & 1.602\times 10^{-12}\ \text{erg} \end{pmatrix}$$

are substituted for the above equation, the wavelength $\lambda$ having a unit in the order of angstroms and the charged voltage having a unit in the order of Kv, there is obtained an equation, $$\lambda\text{min}[\text{Å}]=12.4/V\text{max}[\text{Kv}]$$

If the charged voltage is known, therefore, the wavelength $\lambda$min can be easily calculated. For example, if the charged voltage Vmax is 24.8 Kv, there are generated electromagnetic waves over a wide range, the minimum wavelength thereof being 0.5 angstrom. However, the energy is not all converted. The conversion efficiency $\epsilon$ is given by, $$\begin{aligned}\epsilon &= \frac{\text{Total energy of electromagnetic waves}}{\text{Energy of electron rays}} \\ &= \frac{Z\cdot V^2\cdot I}{V\cdot I}\times K\times 100\ (\%) \\ &= 1.1\times 10^{-9}\ ZV\ (\%)\end{aligned}$$

where,

K: $1.1\times 10^{-9}$

Z: atomic number of the atoms that received impingement

I: discharge current

Therefore, part of the sparks of static electricity caused by the avalanche phenomenon of electrons is converted into electromagnetic waves which, however, is related to extranuclear electrons and have wavelengths longer than those of the X-rays. The range is indicated by a region 101 in FIG. 9.

With a semiconductor in which silicon forms the base, the electrons move freely when they are irradiated with electromagnetic waves or a beam of particles having energy greater than an energy gap $Eg\ (=1.2\ \text{eV})$. In terms of the threshold wavelength, the electrons move freely when they are irradiated with electromagnetic waves having wavelengths shorter than 10331.5 angstroms, since $\nu=E/h$, $\lambda=c/\nu$. The range is indicated by a region 102 in FIG. 9.

Thus, a metal part connected to the potential of the active side 2 serves as an antenna which absorbs electromagnetic waves at the time when the static electricity sparks in compliance with the aforementioned equation $\lambda\text{min}=12.4/V\text{max}$. Therefore, eddy currents flow into the electronic circuit network to produce noise. In the electronic devices, the noise must be suppressed for all of the electromagnetic wave bands (region 104 in FIG. 9). In a grounded circuit, the noise can be suppressed by the single-point grounding for the electromagnetic waves of up to the VHF band that is referred to in a radio communications system, and can be suppressed by the many-point grounding for the electromagnetic waves of the UHF band (region where waveguides are handled), which, however, are not omnipotent. That is, interference to the electronic devices caused by static electricity must be eliminated by a method which does not rely upon the grounding circuit. The region based upon a new concept is indicated by 105 in FIG. 9.

Generally, electrically equivalent constants of a human body consist of a resistance of about one kiloohms and an electrostatic capacity of 200 pF to 500 pF. FIG. 10 shows electrostatic discharge characteristics for the amount of electric charge (Q) when the charged volatage (V) is 20 Kv, resistance (R) is 800 ohms, and electrostatic capacity (C) is 500 pF. The amount of electric charge (Q) is given by, $$\begin{aligned}Q &= C\cdot V \\ &= 500\times 10^{-12}\times 20\times 10^3 \\ &= 10^{-5}\ (C)\end{aligned}$$

If the side in which the discharge takes place has zero resistance, a discharge time $\tau$ given by, $$\tau = C \cdot R$$
$$= 500 \times 10^{-12} \times 800$$
$$= 4 \times 10^{-7} \text{ (sec)}$$

is required until the electric charge of 10 μC is discharged to 1/e. In practice, however, the side in which the discharge takes place has resistance to some extent, and a longer period of time is required for the discharge. If the electric charge passes through the CMOS IC in the electronic circuit network, the oxide film is completely destroyed (scattered). If the device is under an electrically charged condition in which the electric discharge does not take place, the potential of the active side 2 is distributed throughout the electronic circuit network that is constituted relying upon the idea of forming a grounding circuit. Therefore, erroneous input and erroneous operation caused by the electric charge take place on the pull side 3, in the input line 4 and in the field-effect IC.

Harmful influences to the electronic devices caused by the static electricity are summarized below.

(a) The patterns and metallic structural parts on the circuit board connected to the active side 2 function as antennas depending upon the magnitude of energy of the static electricity, and absorb the electromagnetic waves to generate eddy currents which produce noise in the electronic circuit network. In particular, since the portable electronic devices cannot be ideally grounded, the noise energy must be consumed in the electronic circuit network thereby leading to erroneous operation (region indicated by 103 in FIG. 9).

(b) The semiconductor in which silicon forms the base operates erroneously when it is irradiated with electromagnetic waves of a wavelength shorter than 10331.5 angstroms.

(c) The device operates erroneously if the electric charge flows through the electronic circuit network, and the oxide film is broken (scattered) if the electric charge flows through the semiconductor.

(d) The electronic circuit network is affected by the disturbance in the distribution of electric field in which the static electricity exists, when the electronic circuit network is provided with a field-effect IC which, in principle, is susceptible to the electric field.

(ii) Means for Deriving Hypotheses

A semiconductor integrated circuit (IC) chip has many input/output terminals (hereinafter referred to as IC pads). The layout of IC pads will be discussed below. Here, to simplify the description, the layout contains a minimum number of pads. FIG. 11 is a model diagram of the layout of IC pads that are mounted on a circuit board and susceptible to the static electricity. FIG. 13 is is also a model diagram of the layout of IC pads that are mounted on a circuit board and are susceptible to the static electricity. FIG. 12 is a matrix diagram for comparing the positional relations related to the IC pad layout of FIG. 11, and FIG. 14 is a matrix diagram for comparing the positional relations related to the IC pad layout of FIG. 13. The names of coordinates of the matrix are names of the functions of the IC pads. In FIG. 11, for example $X_{IN}$ and $X_{OUT}$ denote IC pads that constitute an oscillation circuit, and $\phi_1$ and $\phi_2$ denote IC pads that constitute a booster circuit. Symbol $V_{DD}$ denotes an IC pad which receives a potential of the active side 2, and $V_{SS}$ denotes an IC pad which receives a potential of the pull side 3. Symbol SW denotes an IC pad of the circuit 1 which is connected to an end of a switch in the input line 4. As for the pads $X_{OUT}$ and $V_{SS}$ located on either side of pad $X_{IN}$ in the model diagram of FIG. 11, symbol ○ is put to the frames of $X_{OUT}$ and in the matrix diagram of FIG. 12 in the row of $X_{IN}$ and $V_{SS}$. Next, as for $X_{IN}$ and SW on side of $X_{OUT}$, symbol ○ is put to the frames of $X_{IN}$ and SW in the row of $X_{OUT}$. Symbols ○ are put to the frames in the same manner as for $\phi_1$, and then as for $\phi_2$, SW, $V_{DD}$ and $V_{SS}$, successively. Similarly, FIG. 14 is described based upon FIG. 13.

Next, a diagram of FIG. 15 for comparing matrixes is described by combining the upper right portion of the diagonal line of the matrix diagram of FIG. 12 which shows the pads that are mounted on the circuit board and are susceptible to the static electricity with the lower left portion of the diagonal line of the matrix diagram of FIG. 14. In FIG. 15, symbols ○ that are located at symmetrical positions relative to the diagonal line are replaced by symbols ●. The matrix of symbols ● indicates that the layouts of IC pads of FIGS. 11 and 13 are in a neighborhood relationship to each other. That is, $X_{IN}$ and $X_{OUT}$, $\phi_1$ and $\phi_2$, and $V_{DD}$ and SW indicate similar layouts having neighborhood relationship in FIGS. 11 and 13. A diagram of FIG. 20 for comparing matrixes is described by combining the upper right portion of the diagonal line of the matrix diagram of FIG. 17 corresponding to FIG. 16 which shows the layout of IC pads that are mounted on the circuit board and are confirmed to be little affected by the static electricity, with the lower left portion of the diagonal line of a matrix diagram of FIG. 19 corresponding to FIG. 18 which shows the layout of IC pads that are confirmed to be little affected by the static electricity after they have been mounted. In FIG. 20, symbols ○ that are located at symmetrical positions relative to the diagonal line are replaced by symboles ●. The matrix of symbols ● indicates that the layouts of IC pads of FIGS. 16 and 18 are in a neighborhood relationship to each other. That is, $X_{IN}$ and $X_{OUT}$, $\phi_1$ and $\phi_2$, and $V_{SS}$ and SW indicate similar layouts having a neighborhood relationship in FIGS. 15 and 17.

The IC that is easily affected by the static electricity after it has been mounted on the circuit board is compared below with the IC that is little affected, in regard to their similar points.

$$\left( \begin{array}{ll} \text{Device easily affected:} & X_{IN} \text{ and } X_{OUT}, \phi_1 \text{ and } \phi_2, \\ & V_{DD} \text{ and } SW \\ \text{Device little affected:} & X_{IN} \text{ and } X_{out}, \phi_1 \text{ and } \phi_2, \\ & V_{SS} \text{ and } SW \end{array} \right)$$

If similar points common to the easily affected IC and the little affected IC are eliminated, since they are irrelevant to whether they are little affected or easily affected, the following fact becomes obvious.

$$\left( \begin{array}{ll} \text{Device easily affected:} & V_{DD} \text{ and } SW \\ \text{Device little affected:} & V_{SS} \text{ and } SW \end{array} \right)$$

The results are discussed below. After mounted on the circuit board, the IC tends to be easily affected or little affected by the static electricity because of the reason that $V_{DD}$ (active side 2) has more patterns that stretch on the circuit board than $V_{SS}$ (pull side 3), since the circuit is designed based upon the idea of employing a grounding circuit. This fact is quite important to derive the following hypotheses.

Hypothesis 1:

The IC which is easily affected has $V_{DD}$ and SW (active side 2 and input line 4) that are adjacent to each other. That is, there exists a large stray capacity Ca between the active side 2 and the input line 4.

Hypothesis 2:

The IC which is little affected has $V_{SS}$ and SW (pull side 3 and input line 4) that are adjacent to each other. That is, a stray capacity Cp between the pull side 3 and the input line 4 is smaller than the above-mentioned stray capacity Ca.

(iii) Experiment to Confirm the Hypotheses:

The following two examples will be described to prove the hypotheses 1 and 2.

FIG. 21 is a diagram of the circuit of a digital wristwatch, in which reference numeral 4a denotes a switch pattern which forms an end of the input line 4, and 2b denotes a switch spring which assumes the potential of the active side 2. On the switch pattern 4a is disposed the switch spring 2b in an opposed manner over an area 9 of 10 mm² maintaining a distance of 0.3 mm, to thereby form an air capacitor. Under this condition, the device is easily affected by the static electricity and operates erroneously for various control operations. If the shape of the switch spring 2b is so changed that it is opposed to the switch pattern over an area 10 instead of the area 9, then the device becomes little affected by the static electricity. This fact verifies the aforementioned hypothesis 1. As a follow-up experiment, a capacitor was inserted between the switch pattern 4a and the potential $V_{SS}$ of the pull side 3 under the condition of the opposed area 9, in order to examine the immunity of the device against the static electricity. It was found that the device exhibited immunity if the capacitor had a capacity greater than a given value.

FIG. 22 is a diagram showing another circuit of the electronic wristwatch. The device is little affected by the static electricity when a temporarily formed $V_{DD}$ pattern 11 is not provided on the $V_{DD}$ pattern 2b adjacent to the switch pattern 4a, the $V_{DD}$ pattern 2b assuming the potential of the active side 2. On the other hand, if the temporarily formed $V_{DD}$ pattern is located adjacent to the switch pattern 4a as shown in the drawing, the device becomes susceptible to the static electricity and operates erroneously such as displaying incorrect indication. This is one of the verifications related to the aforementioned hypothesis 2. The idea to lengthen the pattern of the active side 2 on the circuit board or to increase the area conforms to the way of thinking which is based upon the grounding circuit, but is not quite effective to suppress the noise that stems from the static electricity and rather makes the situation worse.

Even if the existing grounding circuit is employed in an attempt to cope with the static eleciticty, a discharge current of static electricity flows from the metal housing into the electronic circuit network, and the IC is broken down or electrical data in the circuit network are disturbed. Further, electromagnetic waves of large energy generated by lightning or the discharge of static electricity are absorbed by the metal housing and by the pattern of the active side 2 to form eddy currents which then generate noise to disturb the electrical data in the electronic circuit network. Moreover, when the electronic device is placed under a condition where the static electricity is not discharged, the active side 2 (ground side) that spreads throughout the circuit board works more effectively to receive the static electricity than the pull side 3. Therefore, the electric field acts more greatly upon the active side 2 than upon the pull side 3, and the device operates erroneously.

SUMMARY OF INVENTION

The present invention aims at removing the above-mentioned defects that cannot be coped with by the existing idea which is based upon the grounding circuit, and its object is to provide an electronic device that has immunity against the phenomena of static electricity. According to one feature of the present invention, a metal housing contains an electronic circuit which maintains an ordinary potential of the input line by inducing a pull potential on the input line of the electronic circuit network in order to eliminate the induction of active potentials other than an active potential for operating the device, thereby to prevent erroneous inputs from entering thereto. According to the present invention, furthermore, neither the active side (ground side) of the electronic circuit nor the electronic circuit network is permitted to be electrically conductive, in order to interrupt the flow of electric charge and eddy currents produced by the electromagnetic waves of large energy. The housing which is made of an insulating material helps prevent the distribution of electric field from being disturbed in the electronic circuit, and makes it possible to achieve the desired object.

BRIEF DESCRIPTION OF DRAWINGS

FIG. 9 is a diagram to illustrate the concept related to the energy of electromagnetic waves and noise;

FIG. 10 is a diagram of waveforms which represent discharge characteristics of static electricity;

FIGS. 11, 13, 16 and 18 are diagrams of layouts of IC pads for confirming the present invention;

FIGS. 12, 14, 15, 17, 19 and 20 are matrix diagrams of IC pads for confirming the present invention.

DETAILED DESCRIPTION OF THE INVENTION

Figure 1A:
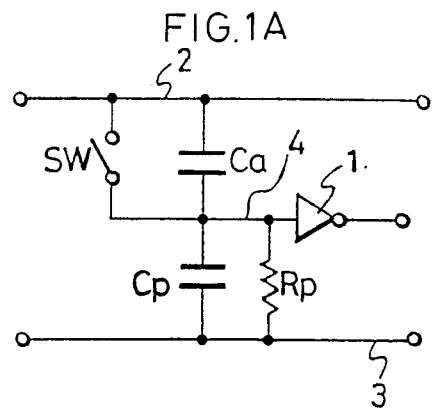
FIG. 1 is a diagram of a fundamental input circuit in an electronic circuit network according to the present invention.
Figure 1B:
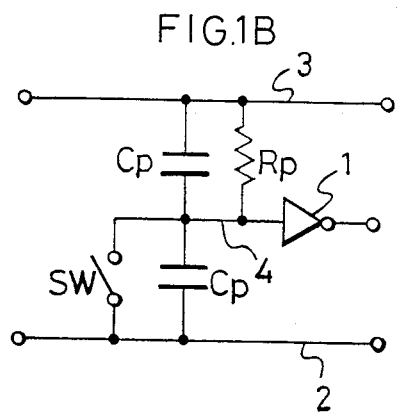

FIG. 1 is a diagram of an input circuit according to an embodiment of the present invention, wherein FIG. 1(A) is a diagram in which the active side 2 assumes a higher potential of the power source voltage, and FIG.

1(B) is a diagram in which the active side 2 assumes a lower potential of the power source voltage. Reference numeral 1 denotes a circuit, 3 denotes a pull side, and 4 denotes an input line. An end of the input line 4 is connected to a switch SW and the other end thereof is connected to the circuit 1. If the switch SW is turned on, the input line assumes the potential of the active side 2 and if the switch SW is turned off, the input line assumes the potential of the pull side 3 via a pull resistance Rp. An electrostatic capacity between the active side 2 and the input line 4 is denoted by Ca and an electrostatic capacity between the input line 4 and the pull side 3 is denoted by Cp, the electrostatic capacities having a relationship Ca<Cp. With the circuit being constructed as described above, even if an impulse is simultaneously superposed on the active side 2 and on the pull side 3 that are power source lines, the potential of the pull side 3 appears on the input line 4 via Cp due to the relationship Ca<Cp. Accordingly, the impulse noise is not induced on the input line 4, and the circuit is prevented from operating erroneously.

Figure 2A:
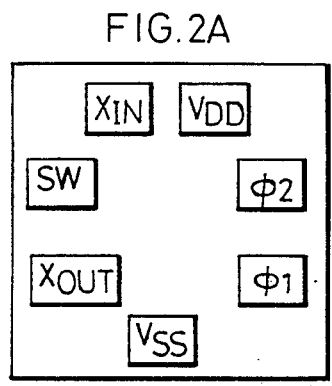
FIGS. 2 and 3 are diagrams of model layouts of IC pads according to the present invention.
Figure 2B:
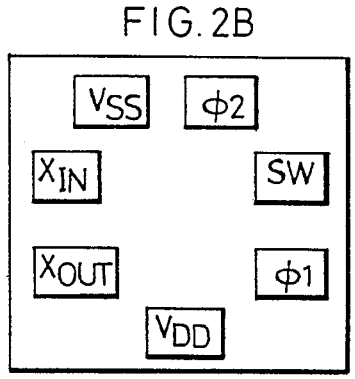

FIG. 2 is a diagram of a model layout of IC pads illustrating important portions only according to another embodiment of the present invention, wherein FIG. 2A is a diagram of a layout of IC pads in a circuit structure in which the active side assumes a higher potential of the power source voltage, and FIG. 2B is a diagram of a layout of IC pads in a circuit structure in which the active side 2 assumes a lower potential of the power source voltage. In FIG. 2A, a terminal (for example, $X_{IN}$ in Figure) other than the pad of $V_{DD}$, other than the pad of SW and other than the input pad for testing, is provided between the pad of $V_{DD}$ (active side 2) and the pad of SW (input line 4). That is, the device is so designed that the stray capacity inevitably decreases between the active side 2 and the input line 4. Namely, the capacity Ca inevitably decreases in the pattern layout on the circuit board. In FIG. 2B, a pad (for example, $\phi_2$ in Figure) other than the pad $V_{SS}$ or SW, and other than the input pad for testing is provided between the pad $V_{SS}$ (active side 2) and the pad SW (input line 4). That is, the device is so designed that the stray capacity inevitably decreases between the active side 2 and the input line 4. Namely, the capacity Ca inevitably decreases in the pattern layout on the circuit board.

Figure 3A:
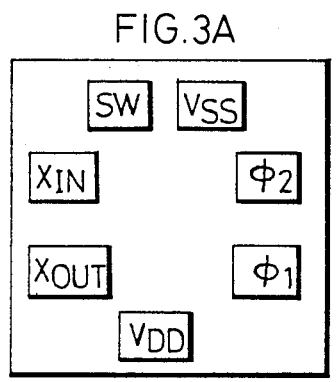
Figure 3B:
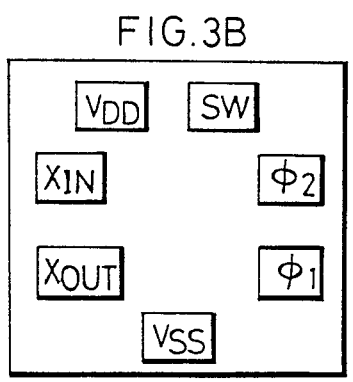

FIG. 3 is a diagram of a model layout of IC pads showing important portions only according to a further embodiment of the present invention, wherein FIG. 3A is a diagram of a layout of IC pads in a circuit structure in which the active side 2 assumes a higher potential of the power source voltage, and FIG. 3B is a diagram of a layout of IC pads in a circuit structure in which the active side 2 assumes a lower potential of the power source voltage. In FIG. 3A, the pad SW (input line 4) is located adjacent to the pad $V_{SS}$ (pull side 3). That is, the device is so designed that the stray capacity is increased as much as possible between the pull side 3 and the input line 4. Namely, the capacity Cp is inevitably increased in the pattern layout on the circuit board.

Figure 4:
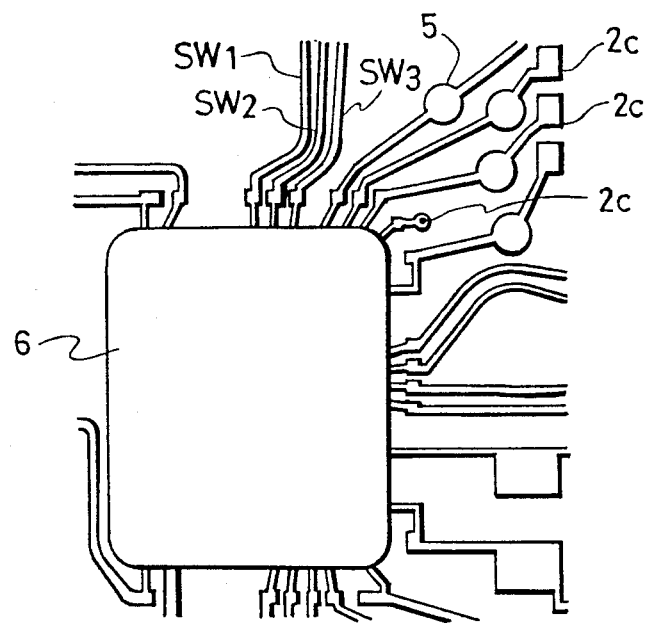
FIGS. 4 and 5 are diagrams illustrating portions of layouts of circuit board patterns according to the present invention.

FIG. 4 is a diagram showing a portion of the layout of circuit board patterns according to a still further embodiment of the present invention, wherein reference numeral 2c denotes active pattern lines, 5 denotes a pattern other than the active pattern lines, other than the SW pattern lines and other than the pattern lines for testing. Symbols $SW_1$, $SW_2$ and $SW_3$ denote switch patterns, and reference numeral 6 denotes an IC chip.

The pattern 5 is formed between the active pattern lines 2c and the pattern $SW_3$, so that the electrostatic capacity Ca decreases inevitably between the active side 2 and the switch pattern $SW_3$ to realize the relationship Ca<Cp mentioned in FIG. 1.

Figure 5:
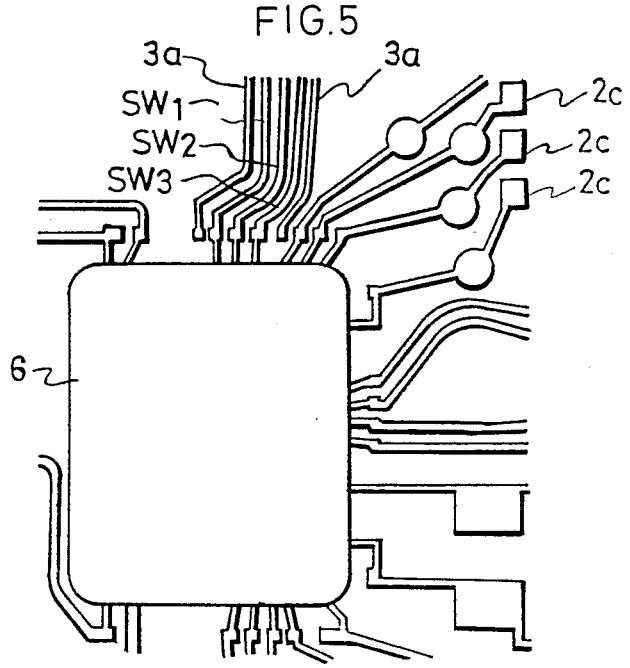

FIG. 5 is a diagram showing a portion of the layout of circuit board patterns according to a yet further embodiment of the present invention, wherein reference numeral 3a denotes pull pattern lines formed adjacent to $SW_1$ and $SW_3$ pattern lines. The electrostatic capacity Cp is inevitably increased between the pull side 3 and the SW to achieve the relationship Ca<Cp mentioned with reference to FIG. 1. In any case, the layout is so designed that the relationship Ca<Cp is maintained in any portion of the pattern lines inclusive of, for example, through-holes.

Figure 6:
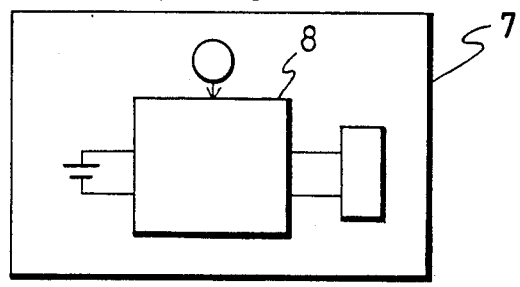
FIG. 6 is a diagram illustrating an electronic circuit network and a metal housing according to the present invention.
Figure 7:
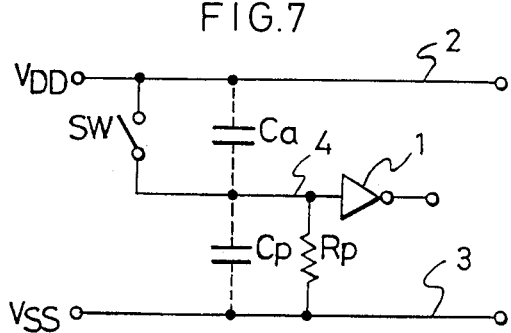
FIG. 7 is a diagram which schematically illustrates the input circuit.
Figure 8:
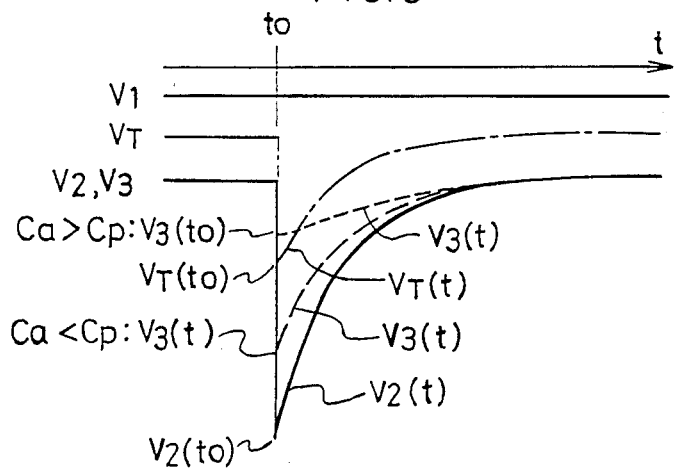
FIG. 8 is a diagram showing voltage waveforms of FIG. 7.
Figures 17, 18, 19, 20:
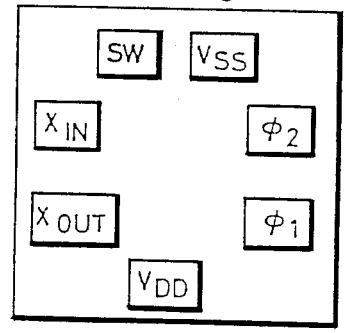
Figure 21:
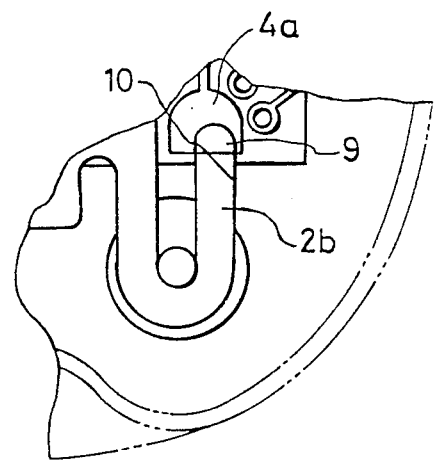
FIGS. 21 and 22 are diagrams of circuit patterns for confirming the present invention.
Figure 22:
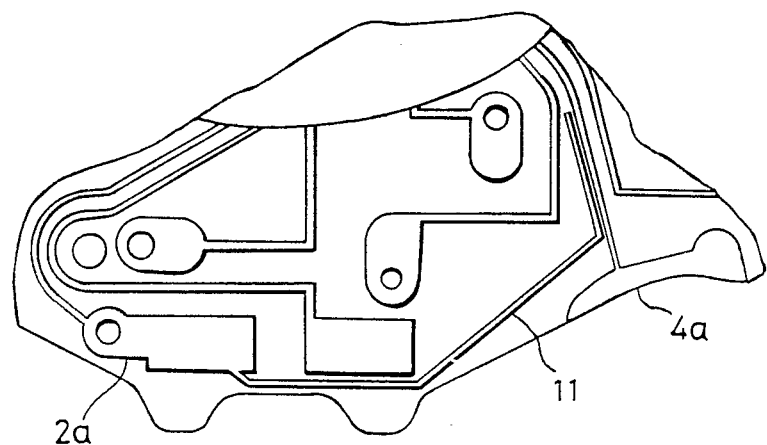

FIG. 6 is a diagram showing the structure of an electronic device in which the electronic circuit network 8 of the present invention illustrated in FIGS. 1, 2, 3, 4 and 5 is contained in the metal housing 7 according to another embodiment of the present invention. Here, if the electrostatic discharge takes place using the metal housing 7 as an electrode, the electric charge migrates by electric quantity stored in the metal housing due to the avalanche of electrons at the time of electric discharge. Here, however, the metal housing 7 is not electrically conducted to the electronic circuit network 8, so that the electric charge will not flow into the electronic circuit network 8. Simultaneously with the electric discharge, furthermore, the kinetic energy of electrons that have impinged upon the metal housing 7 is converted into electromagnetic waves of large energy, and the metal housing 7 works as an antenna to absorb the electromagnetic waves that turn into eddy currents. According to this embodiment, however, the eddy currents are transformed into heat in the metal housing 7 and do not flow into the electronic circuit network 8.

In practice, there are quite a few electronic devices that have the metal housing 7 of the sealed structure. In most cases, therefore, the electromagnetic waves produced by the static electricity fall directly on the electronic circuit network 8. According to the present invention, however, the electronic device is not adversely affected by the phenomena of static electricity owing to the relationship Ca<Cp which is the basis of the present invention. Namely, the embodiments of the present invention completely preclude the afore-mentioned advsese effects (a), (b), (c) and (d) caused by the static electricity from acting upon the electronic devices.

Industrial Applicability

The present invention can be effectively adapted to electronic devices for medical uses and electronic devices to be mounted on aircraft that must not be affected by the phenomena of static electricity, lightning or an external electric field, as well as to electronic devices to be mounted on artificial satellites, for meteorological observations and for atomic utilization that are subject to be exposed to ionizing radiation, corpuscular radiation and charged particles. In the field of civil uses, the invention can be very effectively adapted to robots, IC cards, electronic computers, electronic measuring instruments, electronic cameras, electronic wristwatches and the like.

What is claimed is:

1. In an electronic device: a power source line having a first electric potential; an input line connected at one end thereof to a circuit of the electronic device, said power source line and said input line forming a first capacity (Ca) therebetween; a ground line having a second electric potential, said ground line and said input line forming a second capacity (Cp) therebetween, and said first capacity (Ca) and said second capacity (Cp) maintaining the relation (Ca)<(Cp); said power source line being connected to said input line via a switch through which said first electric potential of said power source line is applied to said circuit; and said input line being connected to said ground line via an impedance element.

2. An electronic device according to claim 1; wherein said impedance element comprises a resistor.

3. In an electronic device having electronic circuitry susceptible of malfunctioning due to the discharge of static electricity: a power source line having a first electric potential; an input line connected at one end to the electronic circuitry and disposed in spaced relation from the power source line to define therebetween a first capacitance; switching means connected to the power source and input line for selectively applying the first electric potential of the power source line to the input line; a ground line having a second electric potential and being disposed in spaced relation from the input line to define therebetween a second capacitance; an impedance element having one end thereof connected to the input line and the other end thereof connected to the ground line; and means for preventing malfunction of the electronic circuitry due to the discharge of static electricty across the power source and ground lines, the means for preventing malfunction comprising positioning the power source line, ground line and input line relative to one another so as to maintain the first capacitance at a value less than the second capacitance.

4. An electronic device according to claim 3; wherein the impedance element comprises a resistor.

5. An electronic device according to claim 3; wherein the electronic circuitry comprises an integrated circuit chip having a first pad connected to the power source line, a second pad connected to the ground line, and a third pad connected to the input line; and the means for preventing malfunction includes positioning the first, second and third pads such that the distance between the first and third pads is greater than the distance between the second and third pads.

* * * * *